United States Patent [19] [11] 4,414,159
Resnick [45] Nov. 8, 1983

[54] VINYL ETHER MONOMERS AND POLYMERS THEREFROM

[75] Inventor: Paul R. Resnick, Wilmington, Del.

[73] Assignee: E. I. Du Pont de Nemours & Co., Wilmington, Del.

[21] Appl. No.: 330,332

[22] Filed: Dec. 14, 1981

Related U.S. Application Data

[62] Division of Ser. No. 191,301, Sep. 26, 1980, Pat. No. 4,334,082.

[51] Int. Cl.$^3$ .................................... C07C 121/130
[52] U.S. Cl. .................. 260/465.6; 560/181; 560/183; 562/583; 562/586; 564/204
[58] Field of Search ............ 260/465.7, 465.8 R, 260/465.6; 526/245, 240, 247; 560/181, 183; 562/583, 586; 564/204

[56] References Cited

U.S. PATENT DOCUMENTS

| | | | |
|---|---|---|---|
| 2,988,537 | 6/1961 | Wiley | 260/67 |
| 3,274,239 | 9/1966 | Selman | 260/514 |
| 3,467,638 | 9/1969 | Pattison | 260/87.5 |
| 3,546,186 | 12/1970 | Gladding et al. | 260/80.73 |
| 3,654,245 | 4/1972 | Kometani et al. | 260/465.7 |
| 3,674,820 | 7/1972 | Pittman et al. | 560/184 |
| 3,933,767 | 1/1976 | Nottke | 260/80.76 |
| 4,131,740 | 12/1978 | England | 560/180 |
| 4,138,426 | 2/1979 | England | 260/465.6 |
| 4,153,804 | 5/1979 | Yamabe et al. | 560/184 |
| 4,273,782 | 6/1981 | Krespan | 260/465.6 |
| 4,275,225 | 6/1981 | Krespan | 560/183 |
| 4,281,092 | 7/1981 | Breazeale | 526/247 |

FOREIGN PATENT DOCUMENTS 861430 6/1978 Belgium .
7707158 11/1978 South Africa .

OTHER PUBLICATIONS

Stacey et al., Advances in Fluorine Chemistry, vol. 3 (1963), pp. 1 and 2.

Primary Examiner—Harry Wong, Jr.
Attorney, Agent, or Firm—James A. Costello

[57] ABSTRACT

Vinyl ether monomers derived from diesters of the formula:

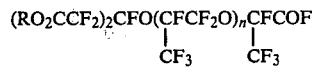

wherein R is $CH_3$ or $C_2H_5$ and n is 0 to 10; copolymers of the vinyl ether monomers with one or more selected perfluorinated monoolefins; articles of manufacture made from the copolymers; process for making the diesters; process for using copolymer membranes in a chlor-alkali cell.

9 Claims, No Drawings

VINYL ETHER MONOMERS AND POLYMERS THEREFROM

CROSS-REFERENCE TO RELATED APPLICATION

This is a division of copending patent application bearing U.S. Ser. No. 191,301, filed on Sept. 26, 1980, now U.S. Pat. No. 4,334,082.

BACKGROUND OF THE INVENTION

This invention relates to vinyl ether monomers derived from dialkyl perfluoro-ω-fluoroformyl esters and to copolymers made therefrom. Following are descriptions of several background developments which provide a context in which to appreciate the present invention.

Krespan, in South African Pat. No. 77/7158, disclosed O=CF($CF_2COD_2CH_3$)$_2$, perfluoroallyl ether dicarboxylates prepared therefrom and perfluorinated copolymers from said dicarboxylates. The perfluoroallyl ether dicarboxylates are neither homologs nor analogs of the perfluorovinyl ether dicarboxylates described herein.

Selman, in U.S. Pat. No. 3,274,239, disclosed fluoroketones of the formula, $XR_FC(O)R'_FX'$, where X and X' are H or halogen and $R_F$ and $R'_F$ are perfluoroalkylene of 1 to 8 carbon atoms; hexafluoropropene oxide (HFPO) adducts thereof, $(XR_F)(X'R'_F)CFO(CF(CF_3)CF_2O)_nCF(CF_3)$ COF, where n is 0 to 20; and vinyl ethers formed from said adducts.

England, in U.S. Pat. No. 4,131,740, disclosed the reaction of HFPO with a compound of the formula FOC—$CF_2$—$CO_2R$ in the presence of fluoride ion as catalyst and an inert liquid diluent (preferably an organic liquid) in which the selected fluoride is at least 0.001% soluble, to form alkyl perfluoro-ω-fluoroformyl esters, $RO_2CCF_2(CF_2O(CF_3)CF)_nCOF$, where n is 0 to 6. Also disclosed are vinyl ethers formed from the esters, and perfluorinated copolymers of the vinyl ethers.

England, in U.S. Pat. No. 4,138,426, disclosed perfluorovinyl ethers, $YCF_2(CF_2O(CF_3)CF)_pCF_2OCF=CF_2$, wherein Y is —$CO_2R$, —$CO_2H$, —$CO_2M$, or —CN; R is 1 to 6 carbons; M is alkali metal, ammonium or quaternary ammonium; and p is 1 to 5.

Breazeale, in U.S. application Ser. No. 083,751, filed Oct. 22, 1979 now U.S. Pat. No. 4,281,092, disclosed vulcanizable copolymers of tetrafluoroethylene, perfluoromethyl perfluorovinyl ether and a cure site monomer consisting of a cyano-substituted perfluorovinyl ether of the formula, $CF_2=CF[OCF_2CF(CF_3)]_x$-$O(CF_2)_nCN$, where n is 1 to 4 and x is 1 to 2.

SUMMARY OF THE INVENTION

This invention concerns vinyl ethers derived from dialkyl perfluoro-ω-fluoroformyl diesters of the formula:

$$(RO_2CCF_2)_2CFO(CFCF_2O)_nCFCOF \quad 1$$
$$\phantom{(RO_2CCF_2)_2CFO(}CF_3\phantom{CF_2O)_n}CF_3$$

wherein R is $CH_3$ or $C_2H_5$ and n is an integer from 0 to 10.

The vinyl ethers have the formula:

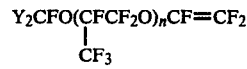

wherein Y is selected from the group consisting essentially of $CF_2CN$, $CF_2CO_2R$, $CF_2CO_2H$, $CF_2CO_2M$, $CF_2CONH_2$ and $CF_2CONR_2$; R and n are as defined above; M is an alkali metal, ammonium or quarternary ammonium.

This invention also concerns copolymers of the vinyl ethers, 2, with one or more perfluorinated monoolefins selected from the group consisting of tetrafluoroethylene, hexafluoropropylene, perfluoroalkylvinyl ethers wherein the alkyl group contains 1 to 4 carbon atoms, chlorotrifluoroethylene, the vinyl ether, $CF_2=CF[OCF_2CF(CF_3)]_mOCF_2CF_2SO_2F$, where m is 1 or 2, and mixtures thereof, said copolymers containing from about 0.1 to 80 mole percent of vinyl ether, 2. This invention also concerns articles of manufacture made from said copolymers, including molded objects and ion-exchange membranes. This invention also concerns a process for producing an alkali metal hydroxide in a chlor-alkali electrolysis cell using an ion-exchange membrane prepared from said copolymers.

This invention also concerns a process for preparing the diesters, 1, by contacting dialkyltetrafluoro-3-oxoglutarate, O=C($CF_2CO_2R$)$_2$, 3, wherein R is $CH_3$ or $C_2H_5$, with hexafluoropropene oxide (HFPO),

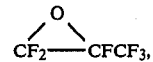

in the presence of fluoride ion as catalyst and a solvent for reactants and catalyst.

DETAILS OF THE INVENTION

The Diester Adducts

The dialkyl-tetrafluoro-3-oxoglutarate, 3, is reacted with HFPO in the presence of fluoride ion as catalyst and a solvent. The fluoride ions are typically provided by one or more of the following sources: an alkali metal fluoride, an ammonium fluoride, a sulfonium fluoride such as benzene sulfonium fluoride and the like. Potassium fluoride is preferred since its use results in improved product yields. The fluoride catalyst can be used in amounts of about 0.01 to 10 equivalents, preferably about 0.05 to 0.5 equivalents, per mole of 3.

Suitable solvents are aprotic liquids or mixtures thereof, including the so-called glymes (mono-, di-, tri- and tetraethyleneglycol dimethyl ether); mononitriles such as aceto-, propio-, butyro- and benzonitrile; dinitriles such as malono-, succino-, glutaro-, adipo-, methylmalono-, pimelo-, subero-, and phthalonitrile; nitrobenzenes; lactones such as γ-butyrolactone, δ-valerolactone and δ-caprolactone. Preferred solvents are mixtures of dinitriles and glymes; especially preferred are mixtures of adiponitrile and tetraglyme in the proportion of about 80 and 98 weight percent of adiponitrile and 2 to 20 weight percent of tetraglyme.

The reaction of ketone, 3, with HFPO is exothermic. Reaction temperatures can range from about 0° to 100° C., with temperatures between 25° and 70° C. being preferred. Pressure is not critical, and subatmospheric and superatmospheric pressures are operable; pressures close to atmospheric are preferred. As illustrated in the Examples, pressure in the reaction vessel is normally controlled by regulating the supply of gaseous HFPO.

Ketone, 3, is preferably present in substantial excess at the beginning of the reaction. The ketone reacts with 1 or more mols of HFPO to form adducts 1 in which n is 0 (1.1 monoadduct), or an integer of 1 to 10. Adducts wherein n=0 or 1 are preferred; adducts wherein n=1 are most preferred. Use of excess ketone, 3, in the reaction improves yields of the desired lower adducts (n=0, 1) as well as overall yields of adducts by suppressing formation of HFPO oligomers which are undesired by-products formed by fluoride ion-catalyzed polymerization of HFPO.

There are several reaction parameters which affect the identity of the particular adduct that is made. Because adduct solubility tends to decrease in a given solvent as the value of n increases, correspondingly better solvents are required to dissolve adducts having high proportions of HFPO. Also, relatively high temperatures and low HFPO pressures (within the parameters described herein) tend to favor production of adducts where n is at the lower end of the range, 0 to 10. On the other hand, to obtain adducts having high n values, it is desirable to employ relatively low temperature and high HFPO pressure.

As explained above, choice of solvent is important relative to the n value of the desired adducts. Thus, to produce adducts having high n values, solvents of relatively high dissolving power should be employed. In this regard, the glymes are better solvents than the nitriles and solvent strength can be adjusted by using mixtures of glymes and nitriles in varying proportions.

Choice of solvent also influences the rate at which adducts, 1, are formed by controlling the amount of catalyst in solution; fluoride ion sources such as potassium fluoride are more soluble in the glymes than in the nitriles. Thus, glyme/nitrile mixed solvents can be tailored for preferred adducts and for optimum reaction rate. Higher rates of adduct formation also improve adduct yields by suppressing the HFPO oligomer-forming side reaction.

To prepare preferred adducts, 1, wherein n=0 or 1, it has been found that the reaction proceeds best when a substantial excess of ketone, 3, over HFPO is used and when a solvent mixture is selected in which the solubility of the desired adduct, and all higher adducts, is relatively low. Under such conditions, the desired adduct product is removed from solution and hence cannot react further with HFPO. In the reaction of ketone, 3, with two moles of HFPO to form the adduct wherein n=1, inevitably the monoadduct (n=0) is also formed as an intermediate and must be at least partly soluble in the reaction mixture so as to react with a further mole of HFPO. The monoadduct so formed may be recycled into the claimed process, either alone or, preferably, in admixture with ketone, 3, as shown in Example 4. Such a mixture may be prepared by adding fresh ketone to the reaction vessel or by recovering the monoadduct and mixing it with a fresh charge of excess ketone and HFPO in a subsequent reaction. Other methods of assuring product optimization will be obvious to one skilled in the art from the description provided herein.

The Vinyl Ethers

The compounds for formula 1 can be pyrolyzed over a solid basic salt such as trisodium phosphate, potassium carbonate, or, preferably, sodium carbonate, to obtain the corresponding polymerizable vinyl ether monomers of formula 2':

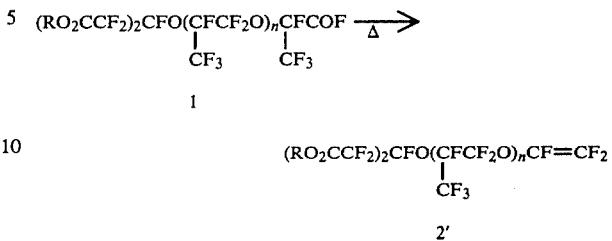

The pyrolysis reaction takes place at temperatures of about 120° to 300° C., preferably 150° to 250° C. in an inert atmosphere, e.g., nitrogen, in the presence of the basic salts which have been previously dried by heating to at least 300° C. The monomeric diesters of formula 2' are converted by known methods into vinyl ether monomers having the following $Y_2$ values:

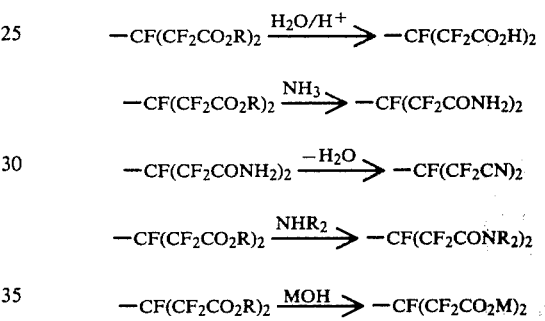

wherein R and M are as previously defined.

Monomers of formula 2 can be copolymerized with one or more of the fluorinated vinyl monomers listed above (tetrafluoroethylene, etc.) to yield solid, tough thermoplastic copolymers which can be molded into shaped articles, including films, and ion exchange membranes for chlor-alkali electrolysis cells. Alternatively, for polymer uses requiring ion-exchange capability, the monomer, 2', can be copolymerized with said fluorinated vinyl monomers and the copolymer subsequently converted by hydrolysis to the corresponding copolymer containing $-CF_2CO_2H$ or $-CF_2CO_2M$ groups. Formula 2 monomers wherein Y is $-CF_2CN$ are especially useful for incorporating cure sites into fluoroelastomer compositions.

It will be understood that the vinyl monomers of this invention contain two especially useful terminal functional groups in addition to the polymerizable vinyl site. Thus, the present monomers make it possible to double the functionality of copolymers derived therefrom without increasing the molar percentage of functional monomers in said copolymers. Alternatively, copolymer functionality can be maintained while only employing half the molar percentage of functional monomer previously necessary.

Copolymers

Copolymers prepared from Formula 2 vinyl monomers contain repeating units having the formula

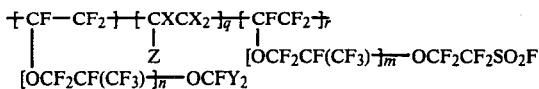

where Y and n are as defined above, m is 1 or 2, q is about 1 to 500, r is 0 or about 1 to 5, Z is $-F$, $-R_F$ or $-OR_F$ where $R_F$ is perfluoroalkyl of 1 to 4 carbon atoms, preferably 1 or 2 carbon atoms, and the X's can all be fluorine or two can be fluorine and one chlorine. Preferred copolymers are those wherein X and Z are $-F$, Y is $-CF_2CO_2R$ or $-CF_2CN$, n is 1 or 2, q is 3 to 500, r is 0 or 1 and m is 1. Values of q from 3 to 20 are preferred for carboxylated copolymers used as electrolysis cell membranes; q of 40 to 400 and r=0 are preferred in nitrile-functional fluoroelastomers. Preferred monolefins for copolymerization with formula 2 vinyl ethers include tetrafluoroethylene, hexafluoropropylene, perfluoroalkylvinyl ethers wherein the alkyl group contains 1 to 4 carbon atoms, chlorotrifluoroethylene, the vinyl ether, $CF_2=CF[OCF_2CF(CF_3)]_mOCF_2CF_2SO_2F$, where m is 1 or 2, and mixtures thereof.

In the following Examples parts are by weight unless otherwise specified. Temperatures are in degrees centigrade.

EXAMPLE 1

Reaction of Dimethyl Tetrafluoro-3-Oxyglutarate With Hexafluoropropene Oxide

Cesium fluoride (10 g., 0.18 mol) in a 2 liter 3-neck flask was heated by a Meker burner under vacuum with swirling to dryness. After cooling, the flask was filled with nitrogen and fitted with a thermometer and large magnetic stirrer. Then, 15 ml of tetraglyme and 19.5 g (0.08 mol) of the above tilted ketoester were added. The flask was evacuated and then automatically maintained at about 700 mm (91 kPa) pressure of HFPO. Vigorous stirring resulted in exothermic (54°) absorption of HFPO which was arbitrarily stopped after 19 g (0.11 mol) had been absorbed. Two liquid layers were present in the reaction mixture after HFPO absorption, indicating reaction products which were insoluble in tetraglyme.

Vacuum (ca. 1.0 mm, 130 Pa) was applied to the flask through a liquid nitrogen-cooled trap while heating the flask with steam. The contents of the trap were distilled and fractions collected boiling from 30°/15 mm (2 kPa) to 82°/0.2 mm (26 Pa). The higher boiling fractions contained two layers due to co-distillation of tetraglyme. The fractions are believed to have contained adducts, 1, wherein n=0 to 10. By-product HFPO oligomers formed, if any, were present in lower boiling fractions not collected.

EXAMPLE 2

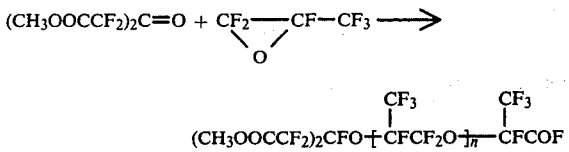

Potassium fluoride (5 g, 0.09 mol) in a 2 liter 3-neck flask was heated by a Meker burner under vacuum with swirling to dryness. After cooling, the flask was filled with nitrogen and fitted with a thermometer and large magnetic stirrer. Then, 2.54 g of tetraglyme (bis[2-(2-methoxyethoxy)ethyl]ether) and 40 ml (48.5 g) of adiponitrile were added, the flask evacuated and flushed again with nitrogen. Dimethyl tetrafluoro 3-oxoglutarate (MKG) (321 g, 1.3 mol) was added and the flask evacuated, filled with HFPO and weighed. Stirring was started and after an induction period of about one hour absorption of HFPO began, reaching a maximum of about 0.6 g/min and a temperature of 37°. HFPO pressure was automatically maintained at about 700 mm (91 kPa). The flask was weighed periodically and addition of HFPO was stopped arbitrarily after 267 g (1.6 mol) had been absorbed.

The contents of the flask were filtered through a sintered glass funnel to remove KF and the filtrate was distilled under vacuum (0.5–1.0 mm; 65 to 130 Pa). There was recovered 79.5 g of HFPO oligomers (mostly dimer and trimer) from the Dry Ice-cooled trap on the still and as bottom layer in the first cuts of recovered MKG. The first cuts boiling up to 78°/0.8 mm (104 Pa) after removing bottom layer amounted to 378 g and were about 50 mol percent of MKG and 50 mol percent (237 g) of monoadduct (n=0), dimethyl 2,2,3,4,4-pentafluoro-3-(1-fluorocarbonyl-1,2,2,2-tetrafluoroethyoxy)-penetanedioate, as analyzed by gas chromatography.

There was then obtained 8.6 g of diadduct (n=1), dimethyl 2,2,3,4,4-pentafluoro-3-[2-(1-fluorocarbonyl-1,2,2,2-tetrafluoroethoxy)-1,2,2-trifluoro-1-(trifluoromethyl)ethoxyl]-pentanediolate, b.p. 86°/1 mm (130 Pa); 12.7 g of triadduct (n=2) dimethyl 2,2,3,4,4-pentafluoro-3-[2,3,3,5,6,6,8,9,9,9-decafluoro-8-fluorocarbonyl-2,5-bis(trifluoromethyl)-1,4,7-trioxanon-1-yl]pentanedioate, b.p. 93°/0.4 mm (52 Pa); 9.0 g of tetraadduct (n=3), dimethyl 2,2,3,4,4-pentafluoro-3-[2,3,3,5,6,6,8,9,9,11,12,12,12-tridecafluoro-11-fluorocarbonyl-2,5,8-tris(trifluoromethyl)-1,4,7,10-tetraoxanon-1-yl]pentanedioate, b.p. 103°/0.4 mm (52 Pa) and 150 g of higher boiling material including adiponitrile. The adiponitrile began to codistill with the adduct and separated from these fractions as a top layer which was removed before the next step. Analytical data and physical properties of the HFPO adducts (n=1,2,3,4) are given in Tables 1 and 2.

EXAMPLE 3

Dimethyl tetrafluoro-3-oxoglutarate (MKG) (124 g, 0.5 mol) was reacted with HFPO as described in Example 2 using 60 ml of diglyme as solvent and 10 g of cesium fluoride plus 3.5 g of potassium fluoride as catalyst. Reaction was exothermic (53°) after an induction period of 2.5 hrs. However, the HFPO absorbed (1099 g, 6.62 mol) was largely converted to HFPO oligomers. There was isolated 45 g of the monoadduct (n=0), b.p 73°/1.4 mm (182 Pa). Physical and analytical data for the monoadduct are given in Tables 1 and 2.

EXAMPLE 4

A mixture of dimethyl tetrafluoro-3-oxoglutarate (MKG) (50 g, 0.2 mol) and its mono-HFPO adduct (50 g, 0.12 mol) were reacted with excess HFPO using 5 g of KF as catalyst and a mixture of 50 g of adiponitrile and 2.6 g of tetraglyme as solvent. After 55 g (0.33 mol) of HFPO had been absorbed the mixture consisted of two layers. The bottom layer was removed and distilled to give about 52 g of a mixture of 8 mol percent of MKG and 92 mol percent (49 g) of monoadduct (n=0); 11 g of diadduct (n=1); and 14 g of triadduct (n=2).

The reaction was restarted after adding 102 g (0.41 mol) of MKG to the top layer and was stopped after absorbing 203 g (1.22 mol) of HFPO. Two layers were again formed. Distillation of the lower layer gave 83 g of a mixture of 2 mol percent of MKG and 98 mol percent (81 g) of monoadduct; 27 g of diadduct; and 45 g of triadduct.

EXAMPLE 5

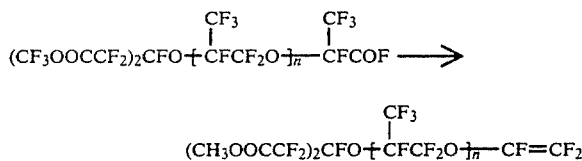

An acid fluoride of the above formula (n=1, 33 ml, 49 g, 0.085 mol) prepared as in Example 2, was added through a syringe driven by a Sage pump at the rate of 0.6 ml/min to a stirred bed of 90 ml of sodium carbonate at 190° (previously dried at 400°) under a slow current of nitrogen. The sodium carbonate was contained in a quartz tube, 2.54 cm diameter ×45.7 cm long, fitted at the top with openings for nitrogen, syringe needle and a motor driven screw running through the bed and heated by a split-type furnace. Product was collected at the bottom of the tube.

When addition was complete, vacuum was applied and there was collected in Dry-Ice—and liquid nitrogen—cooled traps (in series) 38.5 g of material. Distillation gave 23 g of the above vinyl ether (n=1),dimethyl 2,2,3,4,4-pentafluoro-3-[2-(1,2,2-trifluoroethenyloxy)-1,2,2-trifluoro-1-(trifluoromethyl)-ethoxy]pentanedioate, b.p. 77°/0.1 mm (13 Pa). Higher boiling cuts showed the presence of some decarboxylation product [CF(CF$_3$)H] in place of CF=CF$_2$ in the above formula. Physical and analytical data for the vinyl ether are given in Tables 1 and 2.

EXAMPLE 6

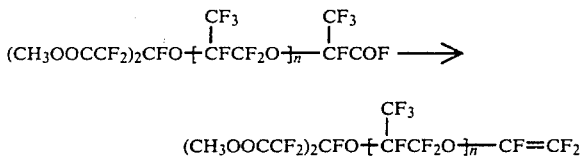

An acid fluoride of the above formula (n=2, 20 ml, 34.5 g, 0.046 mol), prepared as in Example 2, was passed through a stirred bed of 90 ml of sodium carbonate at 202° as described in Example 4. In the same way, 22.5 g was recovered giving on distillation 12 g of the vinyl ether (n=2), dimethyl 2,2,3,4,4-pentafluoro-3[2,3,3,5,6,6,8,9,9-nonafluoro-2,5-bis(trifluoromethyl)-1,4,7-trioxa-8-nonen-1-yl]-pentanedioate, b.p. 87°/0.1 mm (13 Pa). Physical and analytical data for the vinyl ether are given in Tables 1 and 2.

A higher-boiling impurity was largely the decarboxylation product (CF(CF$_3$)H in place of CF=CF$_2$).

EXAMPLE 7

Preparation and Hydrolysis of Copolymer

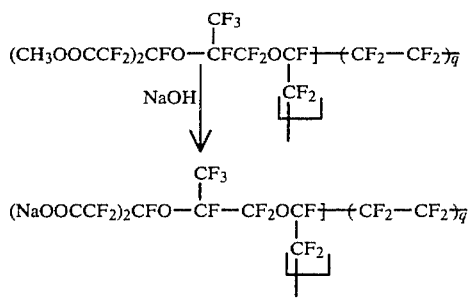

The vinyl ether monomer prepared in Example 5 (n=1, 10.2 g, 0.02 mol), 17.3 g of 1,1,2-trichloro-1,2,2-trifluoroethane (F-113) (distilled under nitrogen), 2.8 g (0.028 mol) of tetrafluoroethylene and 40 µl of perfluoropropionyl peroxide solution (6% in F-113) were sealed in a 20 ml Carius tube (nearly full). After rotating the tube at room temperature overnight, the polymer was rinsed out and washed on a sintered glass funnel with F-113, pressure filtered with nitrogen and vacuum dried in a steam bath to give 1.7 g of white solid. A 7 mil film was pressed at 180° and 5 to 6 mil (0.13–0.15 mm) film at 200°/500 psi (3435 kPa). Infrared spectroscopy of the film showed strong ester carbonyl absorption at 5.6 microns. Infrared spectroscopy of a film removed from aluminum foil by boiling in 10% sodium hydroxide showed broad and strong absorption at 2.9 microns and 5.9 microns for COONa.

Vinyl ether monomer was recovered from the above F-113 solution and redistilled. A Carius tube charge of 8.9 g of vinyl ether, 19.7 g of F-113, 3.4 g of tetrafluoroethylene and 40 µl of perfluoropropionyl peroxide solution treated as above gave 3.2 g of copolymer from which a 7 mil (0.18 mm) film was pressed at 220°/500 psi (3435 kPa).

EXAMPLE 8

In a run similar to that of Example 2, starting with 447 g of a mixture of MKG (35 mol percent) and monoadduct (65 mol percent) recovered from Example 2, in which 90 g of HEPO was absorbed, there was obtained 35 g of HFPO oligomers, 401 g of starting mixture of MKG and monoadduct (35 mol percent of MKG, 65 mol percent of monoadduct (303 g)), 18.1 g of diadduct, 11.4 g of triadduct (n=2), 10.3 g of tetraadduct (n=3) and 92.5 g of higher-boiling material including adiponitrile.

EXAMPLE 9

Potassium fluoride (1.4 g, 0.024 mol) was placed in a 125 ml round-bottom flask fitted with a magnetic stirrer, dropping funnel, Dry Ice-cooled condenser and nitrogen inlet, and "flamed out" under nitrogen with a heat gun. After cooling to 28°, 28.4 g of anhydrous diglyme was added to the flask, followed by slow addition, with stirring, of dimethyl tetrafluoro-3-oxoglutarate (MKG) (29.5 g, 0.12 mol) during which the temperature rose to 33°. Stirring was continued for 1 hr after MKG addition was completed. Almosst all the KF dissolved. The flask was evacuated, then filled with 37 g (0.223 mol) of hexafluoropropene oxide (HFPO). Reaction proceeded at or below 35° for 1.5 h. The reaction mixture, which consisted of two liquid layers, was stirred overnight at room temperature.

The two layers were separated and weighed: total weight, 89.9 g; lower layer, 26.5 g, upper layer, 63.4 g. Vacuum distillation of the upper layer gave two fractions boiling at (1) 84° to 85°/50 mm (29.9 g) and (2) 85° to 90°/10 mm (23.8 g). Gas chromatography, infrared and nuclear magnetic resonance analysis showed fraction (1) to be largely diglyme, and fraction (2) to contain the monoadduct

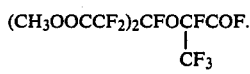

$$(CH_3OOCCF_2)_2CFOCFCOF.$$
$$\qquad\qquad\qquad\quad |$$
$$\qquad\qquad\qquad\;\;CF_3$$

EXAMPLE 10

Potassium fluoride, (5.0 g, 0.09 mol) was added to a 125 ml flask fitted as described in Example 9 and heated under nitrogen. Butyrolactone (45.0 g) and dimethyl tetrafluoro-3-oxoglutarate (MKG) (22.4 g, 0.091 mol) were then added, with stirring, followed by hexafluoropropene oxide (HFPO) (26.0 g, 0.157 mol). Moderately rapid reaction occurred and the temperature rose to 30° to 40°. The reaction mixture consisted of solids and two liquid layers. The solids were filtered off and the liquid layers were separated and weighed: total liquid weight, 89.0 g; lower layer, 65.6 g; upper layer, 23.4 g. Gas chromatographic analysis showed that the lower layer contained unreacted MKG, butyrolactone, HFPO oligomers and compounds of the formula

$$(CH_3O_2CCF_2)_2CFO[CFCF_2O]_n CFCOF$$
$$\qquad\qquad\qquad\qquad\qquad\qquad\quad |$$
$$\qquad\qquad\qquad\qquad\qquad\qquad\;CF_3$$

where n=0, 1, 2 and 3 (mono-, di-, tri- and tetraadducts).

EXAMPLE 11

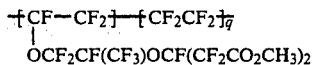

$$\text{-}[CF\text{-}CF_2]\text{-}[CF_2CF_2]_{\overline{q}}$$
$$\;\;\;|$$
$$OCF_2CF(CF_3)OCF(CF_2CO_2CH_3)_2$$

The vinyl ether prepared as in Example 5 (n=1; 16.0 g, 0.031 mol), 1,1,2-trichloro-1,2,2-trifluoroethane (23.5 g), Percadox 16 (bis[4-t-butyl-cyclohexyl]peroxydicarbonate, Noury Chemical Co.; 0.05 g) and tetrafluoroethylene (about 20 g, 0.20 mol) were heated in a stainless steel tube at 45° (4 h), 50° (30 min) and 55° (30 min). The colorless/milky polymeric gel product was washed three times with acetone, filtered and dried in a vacuum oven. The white product weighed 110.1 g. A 2.4 mil film was pressed at 225° from which an infrared spectrum was obtained consistent with that of a copolymer of the above structure.

The copolymer had an equivalent weight of 746 as determined by nuclear magnetic resonance in the following manner at 275°. Signals were obtained in the −79 ppm region, the −115 to −120 ppm region and the −134 ppm region using a CCl₃F standard corresponding to the CF₂O/CF₃ groups, CF groups and OCF groups, respectively. The integrals were 19.0 for the −79 ppm region (CF₂O/CF₃) and 187.5 for the rest of the spectrum. The equivalent weight of the polymer was calculated as follows.

Each comonomer unit contains 5 fluorine atoms in $CF_2O$ or $CF_3$ groups, (a). Thus, each fluorine is equal to 19.0/5=3.8 integral units. The rest of the polymer contains 187.5 integral units arising from other comonomer fluorine atoms and fluorine atoms originally found in tetrafluoroethylene, (TFE). The remaining nine fluorine atoms from the comonomer, (b), are equal to 9×3.8=34.2 integral units. The fluorine atoms arising from TFE are equal to 187.5−34.2=153.3 integral units while those from the comonomer are equal to 34.2+19=53.2 integral units. Therefore, the molar ratio of TFE to comonomer equals $$\frac{153.3/4}{53.2/14} = \frac{38.3}{3.8}$$

or 5.04 moles of TFE per 0.5 mole of comonomer. Since the molecular weight of the comonomer is 484 as the free dicarboxylic acid, the equivalent weight =5.04(100)+484(0.5)=746(or 1.34 meq H+/g). Thus, q in the above formula is 10 (5.04×2).

EXAMPLE 12

Vinyl ethers, $CF_2=CFOCF_2CF(CF_3)OCF_2CF_2SO_2F$, (18.9 g, 0.042 mol), $CF_2=CF[OCF_2CF(CF_3)]_2OCF(CF_2CO_2CH_3)_2$ prepared as in Example 6 (11.2 g, 0.028 mol), Percadox 16 (Noury Chemical Co., 0.05 g), 1,1,2-trichloro-1,2,2-trifluoroethane (46.9 g) and tetrafluoroethylene (about 24 g, 0.24 mol) were heated in a stainless steel tube as described in Example 11. The white polymer product, after washing in acetone, filtering and drying, weighed 23.4 g. A clear film was pressed between Teflon ® plates at 250°. Its infrared spectrum was consistent with that of a terpolymer of the above vinyl ethers and tetrafluoroethylene.

UTILITY

An ion-exchange resin of the copolymer of Example 11 in film form was prepared as follows: 2.0 g of the copolymer, 50 ml of methanol and 7.5 g of potassium hydroxide were placed in a 100 ml round bottom flask fitted with a magnetic stirrer and water-cooled condenser and heated to reflux under nitrogen for 16 h. The flask was then cooled and a gel-like polymer was collected by filtration, washed thoroughly with anhydrous methanol and dried in a vacuum oven. Analysis showed that the polymer was in the form of its potassium (alkali metal) salt. A film of the polymer, pressed at 250° C., was clear.

The carboxyl-functional perfluorinated copolymers of this invention are contemplated for use as cation exchange membranes in chlor-alkali cells. For that utility, the carboxyl-containing membranes would be hydrolyzed to convert the carboxyl groups to the sodium (alkali metal) salt form. In their sodium salt form, the membranes would perform their essential function of permitting migration of sodium cations from the anode compartment to the cathode compartment while preventing the migration of chloride ions from the anode compartment to the cathode compartment.

Vinyl ether monomers of this invention are useful in the vulcanizaton of fluoroelastomers. Copolymerization of vinyl ether monomers of formula 2 wherein Y is CF₂CN with selected perfluorinated monomers such as TFE and perfluoromethylvinyl ether provides curable copolymers which, when heated in the presence of substances known to promote the formation of triazine rings by trimerization of nitriles, become cured (vulcanized) fluoroelastomers.

TABLE 1

INFRARED, BOILING POINT AND ANALYTICAL DATA

A.
$$\begin{array}{c} CH_3OOCCF_2 \\ \phantom{CH_3OOCCF_2} \diagdown \\ \phantom{CH_3OOCCF_2} C \\ \phantom{CH_3OOCCF_2} \diagup \phantom{|} \diagdown \\ CH_3OOCCF_2 \phantom{xx} O{-}[CF{-}CF_2O]_n{-}CFCOF \\ \phantom{CH_3OOCCF_2xxxxxxxxx} | \phantom{xxxxxxxxx} | \\ \phantom{CH_3OOCCF_2xxxxxxxxx} CF_3 \phantom{xxxxxx} CF_3 \end{array}$$

| | | Infrared wave length microns | | | |
|---|---|---|---|---|---|
| Ex. | n | F C=O | OCH₃ C=O | Boiling Point °C./mm (Pa) | Refractive Index $n_D^{25}$ |
| 3 | 0 | 5.30 | 5.55 | 73/1.4 (182) | 1.3468 |
| 2 | 1 | 5.30 | 5.55 | 86/1.0 (130) | 1.3370 |
| 2 | 2 | 5.30 | 5.55 | 93/0.4 (52) | 1.3287 |
| 2 | 3 | 5.30 | 5.55 | 103/0.4 (52) | 1.3230 |

| | Analyses | | | | | | |
|---|---|---|---|---|---|---|---|
| | Calculated | | | Found | | | |
| Ex. | C | H | F | C | H | F | Formula |
| 3 | 29.14 | 1.47 | 46.10 | 29.25 | 1.80 | 46.09 | $C_{10}H_6F_{10}O_6$ |
| 2 | 27.00 | 1.05 | 52.58 | 27.96 | 1.47 | 52.49 | $C_{13}H_6F_{16}O_7$ |
| 2 | 25.82 | 0.81 | 56.17 | 26.69 | 0.93 | 56.27 | $C_{16}H_6F_{22}O_8$ |
| 2 | 25.07 | 0.66 | 58.44 | 24.99 | 0.89 | 59.43 | $C_{19}H_6F_{28}O_9$ |

B.
$$\begin{array}{c} CH_3OOCCF_2 \\ \phantom{CH_3OOCCF_2} \diagdown \\ \phantom{CH_3OOCCF_2} C \\ \phantom{CH_3OOCCF_2} \diagup \phantom{|} \diagdown \\ CH_3OOCCF_2 \phantom{xx} O{-}[CF{-}CF_2O]_n{-}CF{=}CF_2 \\ \phantom{CH_3OOCCF_2xxxxxxxxx} | \\ \phantom{CH_3OOCCF_2xxxxxxxxx} CF_3 \end{array}$$

| | | Infrared wave length microns | | | |
|---|---|---|---|---|---|
| Ex. | n | F C=O | OCH₃ C=O | Boiling Point °C./mm (Pa) | Neut. Equiv. of Acid |
| 4 | 1 | 5.40 | 5.55 | 77/0.2 (13) | 242 |
| 5 | 2 | 5.38 | 5.55 | 87/0.1 (13) | 325 |

| | Analyses | | | | | | | |
|---|---|---|---|---|---|---|---|---|
| | Calculated | | | Found | | | | Mol |
| Ex. | C | H | F | C | H | F | Formula | Wt |
| 4 | 28.14 | 1.18 | 51.94 | 28.78 | 1.43 | 51.87 | $C_{12}H_6F_{14}O_6$ | 512 |
| 5 | 26.56 | 0.89 | 56.03 | 26.54 | 1.02 | 56.12 | $C_{15}H_6F_{20}O_7$ | 678 |

TABLE 2

NUCLEAR MAGNETIC RESONANCE DATA

Proton magnetic resonance spectra were obtained with a Varian A-60 spectrometer operating at 60 MHz; chemical shifts are reported in ppm from tetramethylsilane as external standard with downfield direction taken as positive. $^{19}F$ magnetic resonance spectra were obtained with a Varian A 56/60 spectrometer operating at 56.4 MHz; chemical shifts are reported.

A.
$$\begin{array}{c} CH_3OOCCF_2 \\ \phantom{CH_3OOCCF_2} \diagdown \\ \phantom{CH_3OOCCF_2} C \\ \phantom{CH_3OOCCF_2} \diagup \phantom{|} \diagdown \\ CH_3OOCCF_2 \phantom{xx} O{-}[CFCF_2O]_n{-}CFCOF \\ \phantom{CH_3OOCCF_2xxxxxxxxx} | \phantom{xxxxxx} | \\ \phantom{CH_3OOCCF_2xxxxxxxxx} CF_3 \phantom{xxxx} CF_3 \end{array}$$

| | | Chemical Shifts δ ppm | | | | | |
|---|---|---|---|---|---|---|---|
| Ex. | n | CH₃ | COF | CF₃ | CF₂O | CF₂ (4F) | CF |
| 3 | 0 | 3.70 | +26.98 | −82.16 | | −115.80 | −124.86 |
| | | | | | | | −138.85 |
| 2 | 1 | 3.70 | +26.57 | −79.18 | −79·(1F) broad | −115.84 | −130.55 |
| | | | | −82.15 | −85 (1F) broad | | −135.59 |
| | | | | | | | −138.14 |
| 2 | 2 | 3.67 | +26.41 | −79.21 | −79 (2F) broad | −115.83 | −130.59 |
| | | | | −80.09 | −85 (2F) | | −135.46 |
| | | | | −82.28 broad | | | −138.01 |
| | | | | | | | −145.04 |
| 2 | 3 | 3.65 | +26.30 | −79.33 | −79 (3F) broad | −115.91 | −130.73 |
| | | | | −80.17 (6F) | −85 (3F) broad | | −135.48 |
| | | | | −82.37 | | | −138.73 |
| | | | | | | | −144.91 (2F) |

B.
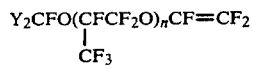

| | | Chemical Shifts δ ppm | | | | | Coupling constants for CF |
|---|---|---|---|---|---|---|---|
| Ex. | n | CH₃ | CF₃ | CF₂O | CF₂ (4F) | CF | $J_{FF}$ in Hz |
| 4 | 1 | 3.68 | −79.32 | −84.06 | −115.93 | −114.68 | 85.6 (d), 65.6 (d) |
| | | | | | | −122.47 | 112 (d), 85.6 (d) 6.2 (t) |
| | | | | | | −136.12 | 112 (d), 65.6 (d) |
| | | | | | | 6.2 (t) | |
| | | | | | | −138.35 | |
| | | | | | | −135.30 | |
| 5 | 2 | 3.68 | −79.20 | −79.48 | −115.81 | −114.55 | 86.8 (d), 66.8 (d), 6.2 (d) |
| | | | −80.14 | −84.69 | | −122.41 | 111 (d), 86.8 (d), 6.0 (t) |
| | | | | | | −136.35 | 111 (d), 66.8 (d), 4.0 (t), 2.0 (d) |
| | | | | | | −135.25 | |
| | | | | | | −138.18 | |

The embodiments of the invention in which an exclusive property or privilege is claimed are defined as follows:

1. A vinyl ether monomer of the formula:

$$Y_2CFO(CFCF_2O)_nCF{=}CF_2$$
$$\phantom{Y_2CFO(}|$$
$$\phantom{Y_2CFO(}CF_3$$

wherein Y is selected from the group consisting of $CF_2CN$, of $CF_2CO_2R$, $CF_2CO_2H$, $CF_2CO_2M$, $CF_2CONH_2$ and $CF_2CONR_2$; R is $CH_3$ or $C_2H_5$; n is an integer from 0 to 10; M is an alkali metal, ammonium or quaternary ammonium group.

2. A vinyl ether monomer according to claim 1 wherein R is $CH_3$.

3. A vinyl ether monomer according to claim 1 wherein R is $C_2H_5$.

4. A vinyl ether monomer according to claim 2 or claim 3 wherein n is 0.

5. A vinyl ether monomer according to claim 2 or claim 3 wherein n is 1.

6. A vinyl ether monomer according to claim 4 where Y is $CF_2CO_2R$.

7. A vinyl ether monomer according to claim 4 wherein Y is $CF_2CN$.

8. A vinyl ether monomer according to claim 5 where Y is $CF_2CO_2R$.

9. A vinyl ether monomer according to claim 5 where Y is $CF_2CN$.

* * * * *